(12) United States Patent
Sukkau

(10) Patent No.: US 12,372,596 B2
(45) Date of Patent: Jul. 29, 2025

(54) MEASUREMENT POSITION ERROR DETERMINATION IN A MAGNETIC RESONANCE DEVICE

(71) Applicant: Siemens Healthineers AG, Forchheim (DE)

(72) Inventor: Johann Sukkau, Herzogenaurach (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 19/011,806

(22) Filed: Jan. 7, 2025

(65) Prior Publication Data

US 2025/0224471 A1 Jul. 10, 2025

(30) Foreign Application Priority Data

Jan. 9, 2024 (DE) ...................... 10 2024 200 167.8

(51) Int. Cl.
*G01V 3/00* (2006.01)
*A61B 5/00* (2006.01)
*A61B 5/055* (2006.01)
*G01R 33/56* (2006.01)

(52) U.S. Cl.
CPC .......... *G01R 33/5608* (2013.01); *A61B 5/055* (2013.01); *A61B 5/702* (2013.01); *A61B 2560/0223* (2013.01)

(58) Field of Classification Search
CPC ............ G01R 33/3607; G01R 33/5608; G06T 11/005; G06T 11/006; G06T 2211/424
USPC ....................................................... 324/309
See application file for complete search history.

(56) References Cited

U.S. PATENT DOCUMENTS

2017/0248665 A1   8/2017 Ludwig et al.

FOREIGN PATENT DOCUMENTS

DE   102016203255 A1 *  8/2007  ........... G01R 33/243

OTHER PUBLICATIONS

Sep. 25, 2024 (DE) Office Action—App. 102024200167.8 (w/English Translation).

* cited by examiner

*Primary Examiner* — Walter L Lindsay, Jr.
*Assistant Examiner* — Frederick Wenderoth
(74) *Attorney, Agent, or Firm* — Banner & Witcoff Ltd.

(57) ABSTRACT

A method for checking the functionality of an MR sensor within a local coil arrangement, the method including: acquiring at a first couch position a first measurement value from the magnetic field sensor outside the bore at the first measurement position of the local coil arrangement, and determining the first position information; acquiring at a second couch position a second measurement value from the magnetic field sensor during or after the conclusion of the couch's travel into the bore at a second measurement position of the local coil arrangement, which second measurement position differs from the first; determining a reference value, which specifies the expected main magnetic field at the second measurement position, determined from the first position information and the couch's displacement distance; and determining error information, which indicates a potential measurement error, by comparing the second measurement value with the reference value.

10 Claims, 3 Drawing Sheets

MEASUREMENT POSITION ERROR DETERMINATION IN A MAGNETIC RESONANCE DEVICE

BACKGROUND

In magnetic resonance imaging, local coil arrangements are often also used that have at least one local coil element that can be used for transmitting and/or receiving and which can be arranged freely onto a patient couch and/or directly on a patient who has been placed on the patient couch. It is then a challenge to move the patient couch into the patient bore of the magnetic resonance device such that the local coil arrangement is placed in the isocenter. The isocenter can be defined to be, for example, the center of the patient bore and/or the center of the homogeneity volume (both locations often coincide). The patient couch is usually moved in a direction that corresponds to its longitudinal direction, which can be denoted as the z-direction. In the case of cylindrical patient bores, the longitudinal direction of the patient couch often corresponds to the field direction of the main magnetic field in the homogeneity volume.

In order to facilitate positioning that is as accurate as possible with regard to the local coil arrangement, it has already been proposed in the prior art to use laser positioning arrangements, in which case, for example, the patient couch with the local coil arrangement must first be adjusted such that a laser marker indicates what is to be placed in the isocenter, after which the couch is automatically moved so that the marked point is brought into the isocenter. For example, a marker laser can be attached for this purpose to the outside of the main magnet unit in a fixed position so that the distance to the isocenter in the z-direction is known. Marker lasers that are variable in position have also been proposed, however. This type of positioning has proved extremely complicated.

Therefore, approaches have also been proposed in the prior art that use as part of the local coil arrangement a magnetic field sensor, which measures the main magnetic field (B0 field), here also comprising the stray field outside the patient bore, at least in terms of its magnetic field strength (preferably in three dimensions based on measurements in three mutually orthogonal directions). Outside the patient bore, i.e., where positioning of the local coil arrangement on the patient takes place, the main magnetic field has a characteristic curve that, in particular, allows a unique association. This means that, using a main magnetic field map (B0 map), it can be deduced from measurement values from the magnetic field sensor, which in particular measures in three dimensions, where the local coil arrangement is located, at least in the z-direction. This position information can be translated easily into a suitable travel path of the patient couch in order to place the local coil arrangement in the isocenter (usually at z=0). For example, DE 10 2016 203 255 A1 describes in greater detail the use of such a magnetic field sensor to determine the position of a local coil arrangement.

It is known in this regard, for example, to display on a touchscreen, in particular, arranged on the main magnet unit adjacent to the patient bore, a schematic representation of at least the patient couch with the local coil arrangements arranged thereon. An operator can then simply tap to select a local coil arrangement, which is then placed automatically in the isocenter ("push-button," also known as "Select and Go"). This allows significantly faster and more convenient positioning.

A Hall sensor, in particular a three-dimensional Hall sensor, is normally used in this context as the magnetic field sensor. Like any other electronic component, a magnetic field sensor also has a limited operating life and may, over time, deliver measurement results that deviate from the actual values or even completely stop working correctly. It is known in this regard that a user of the magnetic resonance device informs a service engineer when this device is indicating a positioning malfunction. This engineer carries out a quality assurance diagnosis on the coil arrangement and, depending on the result, decides whether the local coil arrangement has to be replaced, whether a repair is possible, or the like. The problem with this is that a relatively large amount of time and effort is spent by the user of the magnetic resonance device.

SUMMARY

Therefore, an object of the disclosure is to provide a way of detecting changes in the measurement behavior of magnetic field sensors and hence for servicing in good time.

This object is achieved according to the disclosure by a, in particular, computer-implemented method, a magnetic resonance device, a computer program, and an electronically readable data storage medium, as claimed in the independent claims. The dependent claims contain advantageous developments.

A method of the type mentioned in the introduction has, for the purpose of monitoring that the magnetic field sensor is working correctly, the following steps according to the disclosure:

acquiring for a first couch position of the patient couch the first measurement value from the magnetic field sensor outside the patient bore at the first measurement position of the local coil arrangement, and determining the first position information;

acquiring at a second couch position of the patient couch a second measurement value from the magnetic field sensor during or after the conclusion of travel by the patient couch into the patient bore at a second measurement position of the local coil arrangement, which second measurement position differs from the first measurement position and in particular is located inside the patient bore;

determining at least one reference value, which specifies the expected main magnetic field at the second measurement position, which position is determined from the first position information and the displacement distance of the patient couch between the first and second couch positions given by the position determination device; and determining error information, which indicates a potential measurement error, by comparing the second measurement value with the reference value.

The disclosure makes it possible, instead of reacting to an error, to detect the error proactively and to initiate suitable interventions, for example, a notification to the customer, preferably with a suitable recommendation for action. This makes use of the means of the magnetic resonance device that are present anyway, for example, provided for implementing a "push-button" function, in particular also the facility of being able to ascertain the position of the patient couch accurately at all times by means of a position determination device. In particular, the position of the patient couch is continuously tracked anyway in the control device of the magnetic resonance apparatus in ways known in the prior art. It has now been identified that a single additional measurement by the magnetic field sensor, in particular a Hall sensor, is sufficient for checking that the magnetic field sensor is working correctly.

This is because the magnetic field sensor provides the opportunity to measure the main magnetic field at at least two different points relative to the magnet center (isocenter), since the local coil arrangement is moved with the patient couch. A first measurement of the main magnetic field is performed anyway after placement of the local coil arrangement in the first measurement position in order to determine the first position information from the corresponding first measurement value of the main magnetic field and, hence, also to establish where on the patient couch, at least in the z-direction, is located the magnetic field sensor (first measurement position) and therefore the local coil arrangement. It is thereby possible to determine where the local coil arrangement is located while the patient couch is outside the patient bore (first measurement position). This can be used as is customary for a suitable function, in particular, the "push-button" function described in the introduction.

It is now proposed to perform a new measurement of the main magnetic field at a second measurement position, in particular at the position in which the local coil arrangement or the magnetic field sensor is located when the patient couch has completed its travel along the z-direction into the patient bore. Such an acquisition of a second measurement value at a second measurement position, in particular at the end position of the travel by the patient couch into the patient bore, can be performed quickly and easily, even if it is not needed for the actual function, for instance, "push-button."

Between these two measurements of the main magnetic field lies a large spatial distance of 0.3 to 2.2 m, for example. This leads to a significant difference between the first measurement value and the second measurement value. If the magnetic field sensor is working correctly, then the measurement value to be expected at the second measurement position (reference value) can be predicted from the first measurement by determining the first position information together with the displacement distance of the patient couch (which can be determined by the difference between the second couch position and the first couch position given by the position determination device). If the expectation, i.e., the reference value, is now compared with the second measurement value resulting from the second measurement of the main magnetic field, it is possible to infer therefrom whether the magnetic field sensor is working correctly, which is specified by the error information. The error information can then be interpreted by at least one intervention condition to determine whether an intervention is required.

This check that the magnetic field sensor is working correctly, i.e., the determining of the error information, can be performed particularly advantageously whenever the position detection for the local coil arrangement is active and travel by the patient couch takes place that provides a first measurement position and at least a second measurement position. It is thereby possible to check the functionality and quality of the magnetic field sensor continuously and to act proactively in the event of an error. This dispenses with the need for a dedicated quality assurance step in the service software.

In summary, it can thus be stated that a possible malfunction of the magnetic field sensor can be detected earlier. The user can already be given a notification proactively in very good time, in particular containing a recommendation for action. This means that the user can become active before having to worry about problems that have arisen.

As the magnetic field sensor (also known as a magnetic field strength sensor) is preferably used a magnetic field sensor that measures in three dimensions, in particular a 3D Hall sensor. A significantly better, more robust, and unique position association is possible with a three-dimensional measurement of the main magnetic field. In particular, here, measurements from three orthogonal directions are used to determine the magnetic field strength (also known as the B0 magnitude).

The first measurement value is acquired when the coil arrangement is still outside the patient bore, in particular, at least outside the homogeneity volume. It is, hence, possible to use the main magnetic field map to determine the first measurement position from the first measurement value. In addition, given a movement by the patient couch, there is a difference between the first measurement value and the second measurement value. A corresponding first couch position is also referred to as "close to home" and can be defined, for example, such that the front end of the patient couch does not reach deeper than 30 cm into the patient bore. Thus, the first measurement value, the first position information, and the first couch position are determined at the first measurement position.

If the patient couch has been moved into the patient bore, so in particular, the front end of the patient couch is located deeper in the patient bore than 50 cm, the second measurement of the main magnetic field is performed, i.e., the acquisition of the second measurement value by the magnetic field sensor. Thus, the second measurement value and the second couch position are determined at the second measurement position.

The displacement distance of the patient couch in the z-direction is thus obtained as the difference in the second couch position and the first couch position; the second measurement position (equal to the expected position of the coil arrangement after the travel by the patient couch assuming that the first position information is correct) is then obtained as the sum of the first measurement position, given by the first position information, and the displacement distance.

In order to check whether the magnetic field sensor is working correctly, a reference value is now determined for the second measurement position and is checked to ascertain whether the deviation between the second measurement value and the reference value is sufficiently small.

There are a plurality of ways of actually determining the reference value, in which obviously a plurality of reference values can also be determined and a plurality of comparisons can be carried out in order to achieve as robust a basis as possible for interventions and record-keeping that is as accurate as possible if such record-keeping is carried out.

An expedient development of the present disclosure provides that a first of the at least one reference values is determined from the main magnetic field map at the determined second measurement position. This means that the comparison for a first reference value of this type corresponds to an alignment with the main magnetic field map, which is usually extremely reliable and can generally be assumed to be fundamentally error-free.

It obviously has to be taken into account here that various effects, for instance, the presence of an object under examination and/or other objects, the operating life of the magnetic resonance device, and/or changes in the environment, can also cause changes to occur in the main magnetic field. Such changes in the main magnetic field are often also referred to as B0 drift. In order to be able to sense these changes, it is already known in the prior art to ascertain regularly, for instance, for every magnetic resonance measurement to be carried out, in particular by means of a simple magnetic resonance measurement, a current magnetic resonance frequency, i.e., the Larmor frequency, in the homogeneity volume as a calibration frequency, from which the strength of the main magnetic field in the homogeneity volume can be determined using the gyromagnetic ratio. In order to take into account effects of a drifting main magnetic field also for the main magnetic field map, and hence to avoid errors for the functions that use the main magnetic field map, it is already known to adapt this map, so for instance to correct this map by applying the absolute or relative change to positions outside the homogeneity volume. It is also preferred as part of the present disclosure if the main magnetic field map is corrected before use on the basis of a current calibration frequency measured by a magnetic resonance measurement, which frequency corresponds in particular to the magnetic resonance frequency (Larmor frequency in the homogeneity volume). The magnetic resonance measurement can be carried out as an FID measurement (free induction decay measurement), for example, as is generally known.

If the second measurement position lies inside the homogeneity volume, it can be provided expediently, preferably additionally, that at least a second of the at least one reference value is determined from a calibration frequency or the current calibration frequency measured by a magnetic resonance measurement, which frequency corresponds to the magnetic resonance frequency in the homogeneity volume. If it is known that the magnetic field sensor is located in the homogeneity volume for the second measurement, a second reference value can be determined easily from the current calibration frequency and the gyromagnetic ratio. In the homogeneity volume, it is therefore known very accurately what B0 magnitude the second measurement of the main magnetic field should deliver, in particular also, regardless of an above-discussed correction to the main magnetic field map based on the calibration frequency outside the homogeneity volume.

It should also be mentioned at this point that a second measurement in the homogeneity volume is also particularly preferred in the sense that even with relatively small deviations in position, for instance, because the first measurement value has been measured incorrectly, the expected field strength of the main magnetic field remains the same, and therefore any deviation can be assessed particularly well.

Particularly advantageously, at least for a second measurement position in the homogeneity volume, both the first reference value and the second reference value can be used for the assessment and can form the basis for comparison. This results in a more robust check and in additional information for the assessment of potential error states and trends over time. In particular, a distinction can be made here between situations so that, for example, outside the homogeneity volume, only the first reference value is used, whereas, inside the homogeneity volume, a comparison is made with both the first and second reference values. With regard to additional information, it has been found that, for example, the comparison with the second reference value can allow a better assessment of how well the magnetic field sensor is calibrated and whether the calibration is changing.

It is also conceivable to prioritize the comparisons, for instance only performing a comparison with the second reference value for a plausibility check and/or to obtain further information when the comparison with the first reference value has indicated an error situation. It can also be provided that when using the first and second reference values, the comparison with the second reference value is performed only when a result of the comparison with the first measurement value indicates no measurement error. It is thus possible to adapt to the specific needs for plausibility-checking, robustness, and information.

Obviously exemplary aspects are also conceivable in which only the second reference value is used (at least in the homogeneity volume).

In specific aspects of the present disclosure, it can generally be provided that in the comparison, an absolute or relative deviation of the second measurement value from the reference value is determined, wherein a measurement error is detected if the deviation exceeds a limit value. Whether to consider an absolute or relative deviation can depend here on the reference value. In a specific exemplary aspect, for a nominal field strength of the main magnetic field of 1.5 T, for example, a limit value in the range of 0.08 to 0.12 T, in particular 0.1 T, can be used for the absolute deviation, in particular with respect to the first measurement value. In general, suitable limit values can be determined experimentally at the relevant magnetic resonance device and may turn out to be different depending on the magnetic resonance device/nominal field strength.

In this context, when using the second reference value, a relative deviation can be determined expediently for the second reference value. In the specific exemplary aspect already mentioned, for a nominal field strength of the main magnetic field of 1.5 T, a limit value in the range of 0.05 to 0.09 (i.e., 5 to 9%) has been shown experimentally to be expedient for the relative deviation with respect to the second measurement value.

As already stated, it can be provided particularly advantageously that the error information is interpreted by at least one intervention condition and an assigned intervention is carried out when this condition is satisfied. For example, it can be provided specifically that when error information indicates a measurement error, for instance, when at least one limit value is exceeded, a visual and/or audible notification output about the measurement error is output, in particular jointly with a recommendation for action. A recommendation for action can relate to a repair to be carried out and/or to replacement of the local coil arrangement to be carried out, for example. Other intervention conditions can lead initially just to an entry in an error memory, for example in the case of smaller deviations. In this regard, for example, at least one intervention condition can also be used to monitor whether there is a plurality of successive entries in the error memory in order then also to trigger a notification output as an intervention.

It has proved particularly advantageous as part of the present disclosure, however, to log the error information. This means entering each determined item of error information in a log file. This information can be used for long-term monitoring, for instance, by determining trends and such. In particular, the error information from the present disclosure can be collected and interpreted jointly with further information acquired during field use of the magnetic resonance device in order to develop further the magnetic resonance device and/or to advance or establish the need for new developments.

The first position information can be used, as already mentioned, for implementing various functions in the magnetic resonance device, as is generally known. For example, the position information can be incorporated into the determining of a representation that indicates the local coil arrangements on the patient couch with their position. In addition, the control device can also be designed to drive the patient couch to move into the patient bore depending on the first position information.

Specifically and particularly preferably, it can be provided that after a user has selected one of the at least one local coil arrangement, this is arranged in an isocenter of the magnetic resonance device, which is located in the homogeneity volume, by moving in the patient couch on the basis of the first position information for this local coil arrangement. This considerably simplifies the positioning of local coil arrangements in the isocenter of the magnetic resonance device, for instance, as a "push-button" function. In particular, a representation can be generated that indicates, in particular schematically, currently used local coil arrangements and their position on the patient couch given by the associated first position information. This representation can be output, for example, on a touchscreen or otherwise in such a way that a user can select one of the local coil arrangements to be placed in the isocenter.

It should be mentioned at this point that the determining of the error information, as already mentioned, can preferably be performed for each such positioning process. It can be provided in particular that the error information for each user selection and positioning of a local coil arrangement is determined for all the local coil arrangements. The determining of the error information, therefore, does not have to be confined to the selected local coil arrangement but can concern all the local coil arrangements, in particular, can also concern, when using the first reference value, those that are not placed inside the homogeneity volume.

The disclosure relates not only to the method but also to a magnetic resonance device, having:
- a main magnet unit having a main magnet for producing a main magnetic field, and a, in particular cylindrical, patient bore, wherein the field lines of the main magnetic field in a homogeneity volume in the patient bore run in a field direction;
- a patient couch for moving a patient into the patient bore along a z-direction, which corresponds to the longitudinal direction of the patient couch, wherein, assigned to the patient couch, is a position determination unit for determining a couch position along the z-direction;
- at least one local coil arrangement for placement on the patient and/or the patient couch, wherein the local coil arrangement has a magnetic field sensor, in particular a Hall sensor, for measuring measurement values at least of the magnetic field strength of the main magnetic field; and
- a control device, which is designed to determine first position information for the local coil arrangement, which first position information specifies a first measurement position, by aligning a first measurement value from the magnetic field sensor with a main magnetic field map at least outside the patient bore, which is characterized in that the control device is designed to perform a method according to the disclosure.

All the statements relating to the method according to the disclosure can be applied analogously to the magnetic resonance device according to the disclosure, and therefore, the aforementioned advantages can likewise be achieved by said device. The control device can comprise, in particular, at least one storage means and at least one processor. Functional units, in particular for performing steps of the method according to the disclosure, can be formed by hardware and/or software.

Specifically, the control device can comprise, for example:
- a measurement unit for acquiring the first and second measurement values by suitable driving of, and receiving from the magnetic field sensor;
- a first measurement position determination unit for determining the first position information from the first measurement value and the main magnetic field map;
- a couch position determination unit for determining the couch position by means of the position determination device;
- a second measurement position determination unit for determining the second measurement position from the first position information and the couch position;
- a reference value determination unit for determining the reference value; and
- a comparison unit for determining the error information.

Further functional units can be, for example, an intervention unit for checking intervention conditions and for carrying out the relevant interventions, an output unit for notification output, a user interaction unit for receiving user inputs/outputting representations, and a couch control unit for driving the patient couch (or actuators that propel the couch) to travel into and out of the patient bore. If the control device is also designed to control the remaining operation of the magnetic resonance device, in particular the acquisition operation, there can also be provided, as is generally known, a sequence unit for controlling the acquisition operation, a reconstruction unit for determining magnetic resonance image datasets, and the like.

A computer program, according to the disclosure, can be loaded directly into a storage means of a control device of a magnetic resonance device and comprises program means which, when the computer program is executed on the control device, cause this to perform the steps of a method according to the disclosure. The computer program can be stored on an electronically readable data storage medium according to the disclosure, which therefore has control information stored thereon that comprises at least one computer program according to the disclosure and is configured such that when the data storage medium is used in a control device of a magnetic resonance device, this device is designed to perform a method according to the disclosure. The data storage medium may be, in particular, a non-transient data storage medium, for instance, a CD-ROM.

DESCRIPTION OF THE DRAWINGS

Further advantages and details of the present disclosure are presented in the exemplary aspects described below and with reference to the drawings, in which.

DETAILED DESCRIPTION

Figure 1:
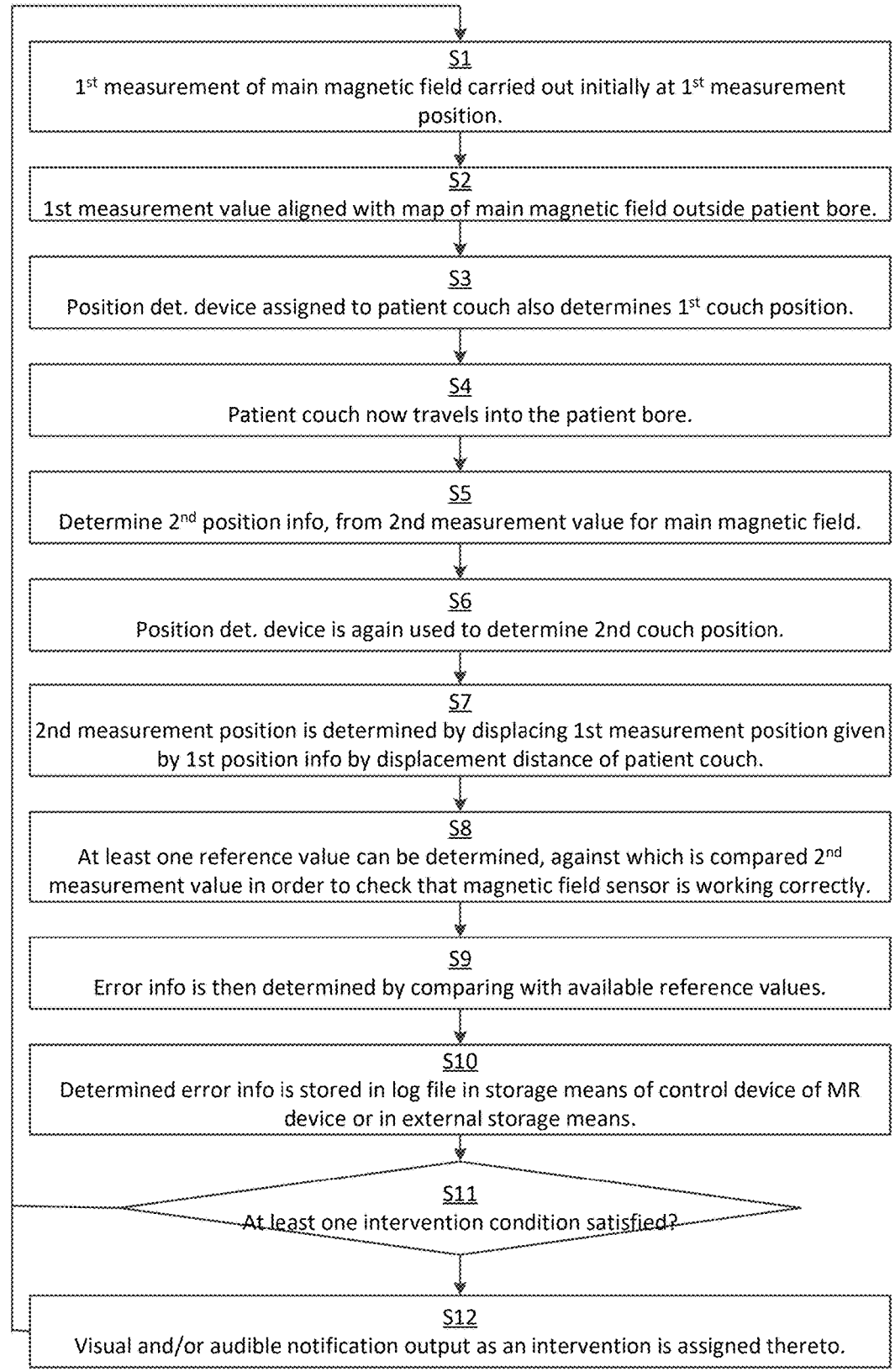
FIG. 1 is a flow diagram of an exemplary aspect of the method according to the disclosure.

FIG. 1 shows a flow diagram of an exemplary aspect of the method according to the disclosure for monitoring the working of a magnetic field sensor, here a Hall sensor that measures in three dimensions, of a local coil arrangement of a magnetic resonance device. If the local coil arrangement is arranged on a patient couch and/or a patient who is placed on the patient couch while the patient couch is situated in a position that is extended out of the patient bore of the magnetic resonance device, then the local coil arrangement is located outside the homogeneity volume of the magnetic resonance device. The patient couch can travel along a z-direction, which corresponds to its longitudinal direction and which, in the present case, also corresponds to the field direction of the main magnetic field (B0 field) in the homogeneity volume. The magnetic field sensor can measure the main magnetic field (B0 field) of the magnetic resonance device, and a control device can determine from a corresponding measurement value, using a main magnetic field map, position information that specifies the current position of the local coil arrangement at least with respect to the z-direction. Such first position information, which is determined at a first measurement position of the local coil arrangement outside the homogeneity volume, can be used in the present case, in particular as part of a "push-button" function, to achieve targeted travel of the patient couch such that the local coil arrangement is positioned in the isocenter of the magnetic resonance device.

Performing said targeted travel by measuring at the first measurement position is also used in the present case, however, as a simple and inexpensive way to check the working of the magnetic field sensor.

To this end, in step S1, the first measurement of the main magnetic field, which measurement is required anyway for operation, is carried out initially at the first measurement position. The result is a first measurement value of the main magnetic field, in particular at least of its amplitude (field strength).

In a step S2, the first measurement value is aligned with a map (corrected on the basis of a currently measured calibration frequency) of the main magnetic field also outside the patient bore in order to determine the corresponding first measurement position and hence the first position information for the local coil arrangement.

Figure 2:
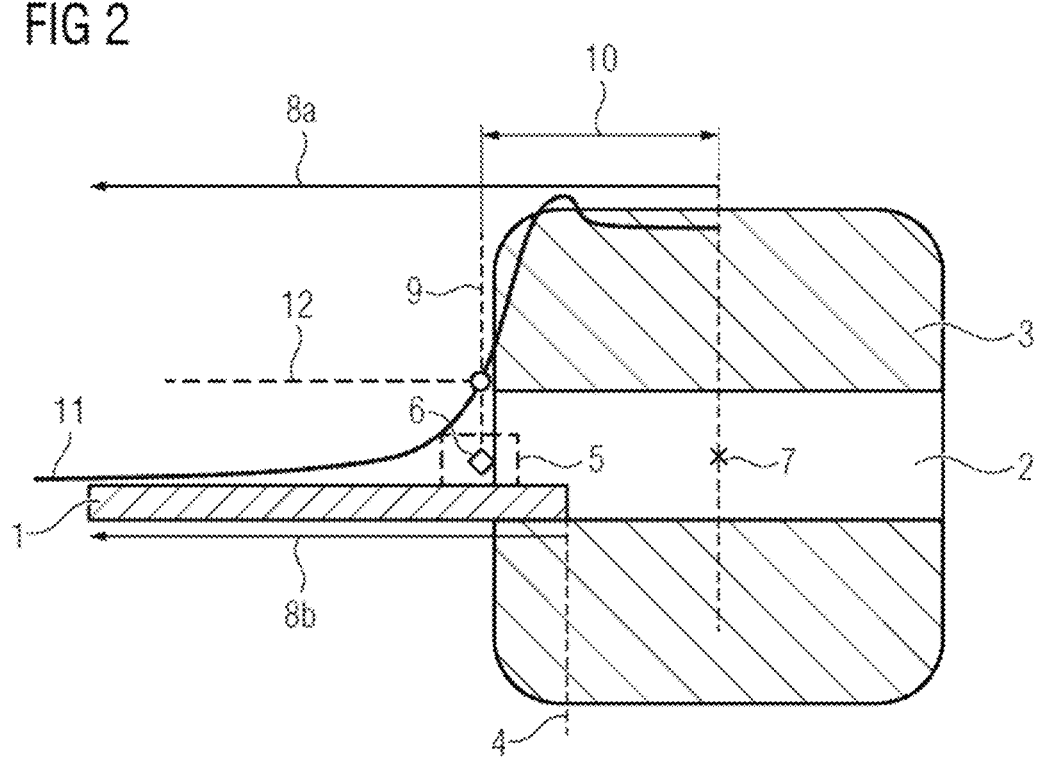
FIG. 2 shows an illustration for the measurement at a first measurement position.

FIG. 2 shows schematically in this regard the situation in the first measurement position. The patient couch 1 is located in an extended first couch position 4, mostly outside the patient bore 2 in the main magnet unit 3. This is known as a close-to-home position, or rather, the patient couch 1 reaches no further than 30 cm into the patient bore 2.

Therefore, a local coil arrangement 5, which is arranged on the patient couch 1 or on a patient (not shown) placed on the patient couch 1, together with a magnetic field sensor 6, here a Hall sensor that measures in three dimensions, is also still situated outside the homogeneity volume around the isocenter 7, which in the present case also defines the origin of the z-direction 8b, which here also corresponds to the field direction 8a. The magnetic field sensor 6 is located at a first measurement position 9 at a distance 10 from the isocenter 7.

The schematic diagram also shows superimposed the curve 11 of the strength of the main magnetic field. At the first measurement position 9, the magnetic field sensor 6 therefore measures, assuming a correct measurement, a first measurement value 12 of the main magnetic field. Since the curve 11 is known from the main magnetic field map, the first measurement position 9 can be determined from the first measurement value 12, and here is stored as the first position information.

Returning to FIG. 1, in a step S3, a position determination device assigned to the patient couch 1 also determines the first couch position 4. The accurate, robust determination of the couch position 4 can be based on relevant feedback from the actuators for moving the patient couch 1 along the z-direction 8b, on the drive history and/or dedicated encoders. The position determination device comprises corresponding sensing means.

In a step S4, the patient couch 1 (with the local coil arrangement 5 fixed in position thereon) now travels into the patient bore 2. The reason for this travel may be, for example, the use of a function for positioning the local coil arrangement 5 in the isocenter 7. In the present case, in order to achieve this function, for instance, in the form of a "push-button" function, a representation is generated based on the first position information for all the local coil arrangements 5 arranged on the patient couch 1, for example, a schematic representation of the local coil arrangements 5 on the patient couch 1. This is output on a touchscreen, which can be arranged, for example, on a casing of the main magnet unit 3 at the end from which the patient couch 1 enters. By selecting one of the local coil arrangements 5, or a control representing this, a user can select the local coil arrangement 5 that is moved into the isocenter 7 by suitable driving of the actuators of the patient couch 1 on the basis of the known distance 10 from the isocenter 7.

Figure 3:
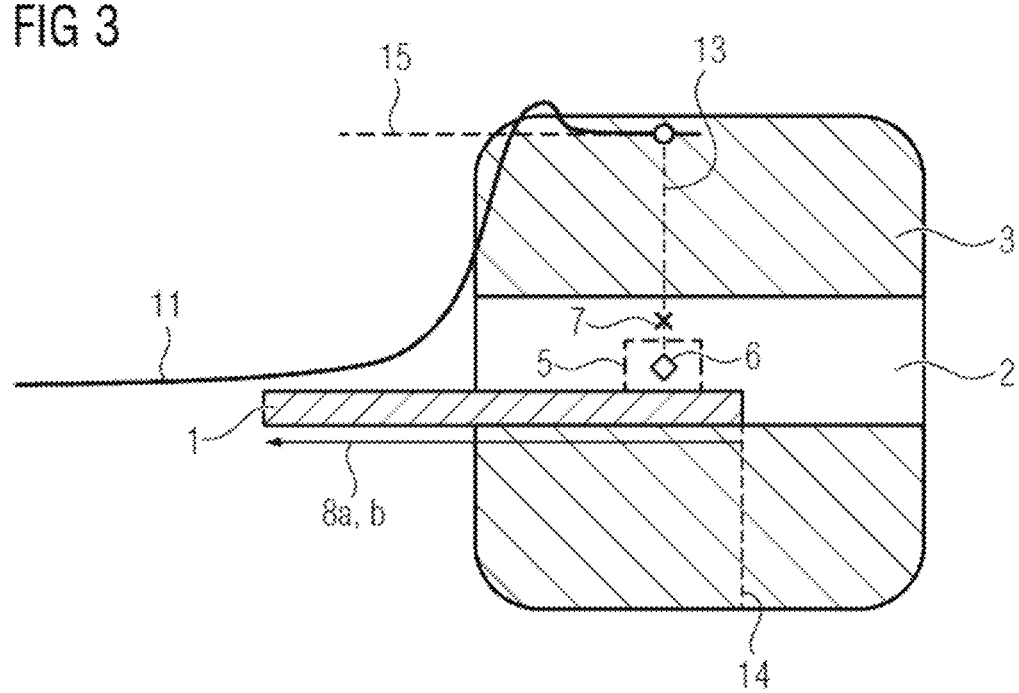
FIG. 3 shows an illustration for the measurement at a second measurement position.

FIG. 3 shows schematically the corresponding situation arising after the end of travel. It can be seen that the magnetic field sensor 6 is now located at a second measurement position 13, which corresponds to the isocenter 7, although this need not necessarily be the case. The patient couch 1 is located, therefore, at a second couch position 14, which is displaced with respect to the first couch position 4 by the distance 10.

Thus, the local coil arrangement 5 and, with it, the magnetic field sensor 6 is now located in the homogeneity volume of constant magnetic field strength, again illustrated by the curve 11, so that it is not reasonably possible to ascertain uniquely a position, i.e., to determine second position information, from the second measurement value 15 for the main magnetic field, which is acquired in a step S5 according to FIG. 1.

In the present case, however, this second measurement is still performed in order to check the working of the magnetic field sensor 6. For this purpose, in a step S6, the position determination device is again used to determine the second couch position 14.

In a step S7, as preparation for determining the reference value, the second measurement position 13 is determined by displacing the first measurement position 9 given by the first position information by the displacement distance of the patient couch 1 (which is obtained directly from the difference between first and second couch positions 4, 14). In the present case, this second measurement position 13 lies inside the homogeneity volume.

In a step S8, then at least one reference value can be determined, against which is compared the second measurement value 15 in order to check that the magnetic field sensor 6 is working correctly. Thus the reference value here corresponds to the expectation based on the second measurement position 13, as was determined in step S7.

In the present exemplary aspect, a first reference value is always determined by retrieving the expected main magnetic field from the main magnetic field map (corrected on the basis of the calibration frequency as described above) at the second measurement position 13. For this first reference value, a comparison is thus provided with the value that is expected based on the main magnetic field map. In addition, however, a distinction between situations is made in step S8.

Only when the second measurement position 13 is located inside the homogeneity volume is a second reference value also determined from the calibration frequency, which originates from a present measurement and equals the magnetic resonance frequency in the homogeneity volume by simply dividing by the gyromagnetic ratio.

In a step S9, error information is then determined by comparing with the available reference values. For the first reference value is ascertained a first, here absolute, deviation, i.e. the magnitude of the difference between the first reference value and the second measurement value 15. An error situation, i.e., an incorrect measurement, can be identified if the first deviation is greater than a first limit value, here by way of example, for a nominal field strength of the main magnetic field of 1.5 T a first limit value of 0.1 T. Both the first deviation and the result of the comparison with the limit value are stored in the error information.

If the second measurement position 13 is located inside the homogeneity volume, then a second reference value is also available, for which a second deviation, here a relative deviation, is determined. This means that the second deviation is determined as the magnitude of the reference of the second reference value and the second measurement value 15 divided by the second reference value. If this second, relative deviation is greater than a second limit value, here by way of example for the above-mentioned case 0.07 (i.e. 7%), once again an error situation can be identified. Both the second deviation and the comparison result are again stored in the error information.

It should be mentioned here that exemplary aspects are also conceivable in which only the second reference value alone is used for the second measurement position 13 in the homogeneity volume. In addition, graduated comparisons, in particular with a plurality of first and/or second limit values, are conceivable.

In a step S10, the determined error information is stored in a log file in a storage means of the control device of the magnetic resonance device or in external storage means, in particular together with further operating data from the magnetic resonance device. It can be provided from there for later analysis.

In a step S11, a check is then made to ascertain whether at least one intervention condition is satisfied. Each intervention condition is assigned an intervention. For example, an intervention condition can check whether one or both of the comparisons indicate that the first and/or second limit value is exceeded. Assigned thereto can then be a visual and/or audible notification output as an intervention, which is to be carried out in step S12 and which is also associated with a recommendation for action, in this case, replacing the local coil arrangement 5. Other intervention conditions can check, for example, whether or not an entry is meant to be made in an error memory.

If no intervention condition is satisfied, or all the associated interventions have been executed, a return is made back to step S1 for the next targeted travel, i.e., the next use of the positioning function using the magnetic field sensor 6. In other words, the check that the magnetic field sensor 6 is working is carried out every time the first position information is determined, followed by travel by the patient couch 1 into the patient bore 2.

It should be reiterated at this point that the second measurement position 13 need not necessarily lie in the homogeneity volume because a check that the magnetic field sensor 6 is working is still possible since an expectation of the second measurement value 15 is again obtained from the main magnetic field map.

Figure 4:
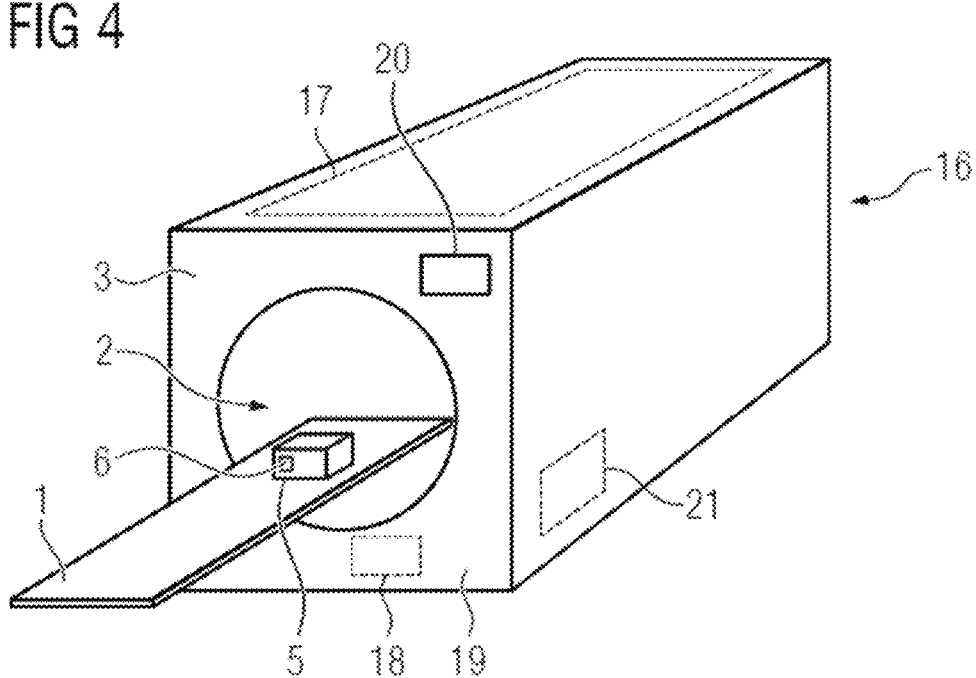
FIG. 4 shows a magnetic resonance device according to the disclosure.

FIG. 4 shows a block diagram of a magnetic resonance device 16 according to the disclosure. This comprises, as already indicated in the block diagrams of FIG. 2 and FIG. 3, a main magnet unit 3 having a cylindrical patient bore 2, into which the patient couch 1 can be moved. The main magnet unit 3 also comprises the main magnet (only outlined here) in the form of a superconducting or permanent magnet 17.

Also outlined is the position determination device 18 for determining the couch position of the patient couch 1. A representation of the patient couch 1 together with the local coil arrangements 5 arranged thereon can be output on a touchscreen 20, which is mounted on the end face 19 of a casing of the main magnet unit 3, in order to make local coil arrangements 5 selectable for positioning in the isocenter 7 through interaction with the representation and/or controls.

Figure 5:
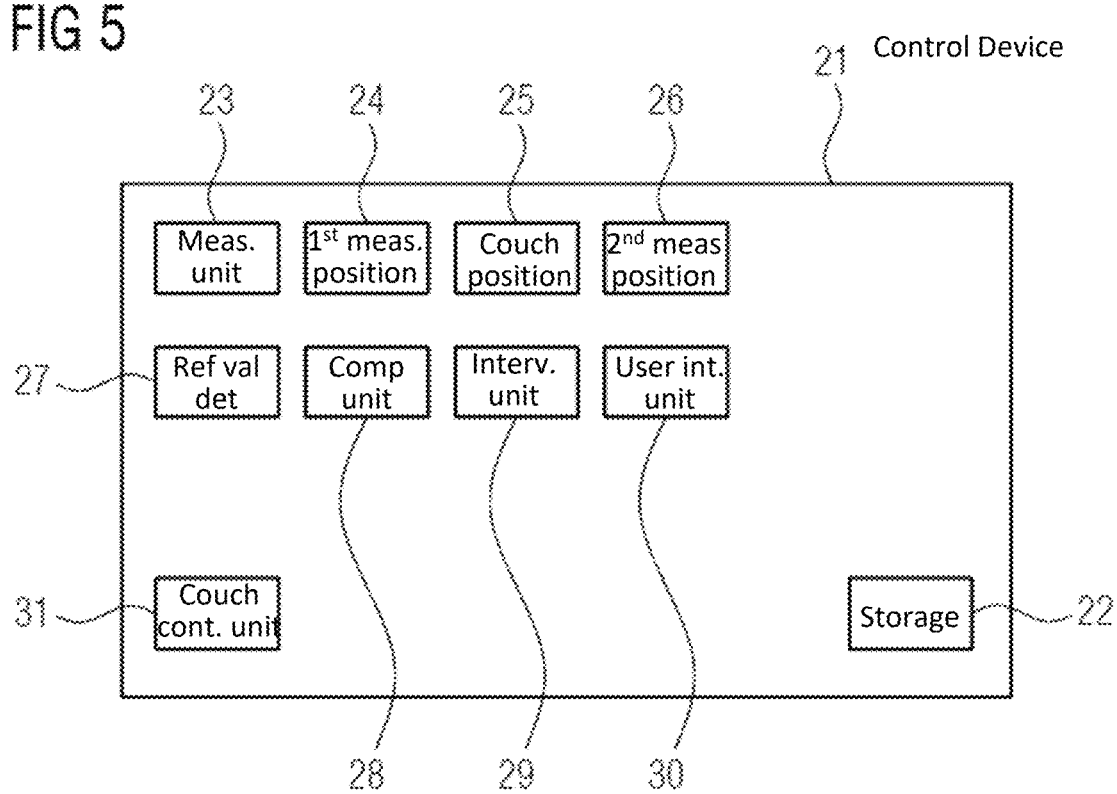
FIG. 5 shows the functional design of a control device of the magnetic resonance device.

The operation of the magnetic resonance device 16 is controlled by a control device 21. The functional design of the control device 21 for performing the method of FIG. 1 is shown in greater detail in FIG. 5 with reference to this method.

According to the figure, the control device 21 first comprises storage means 22, in which can be stored a variety of information, including relating to the method. In addition, the control device 21 comprises a measuring unit 23 for acquiring the first and second measurement values 12, 15 in accordance with steps S1 and S5, a first measurement position determination unit 24 for determining the first position information from the first measurement value 12 and the main magnetic field map in accordance with step S2, a couch position determination unit 25 for determining the first and second couch positions 4, 14 in accordance with steps S3 and S6, a second measurement position determination unit 26 for determining the second measurement position 13 from the first position information and the couch positions 4, 14 in accordance with step S7, a reference-value determination unit 27 for determining the at least one reference value in accordance with step S8, and a comparison unit 28 for determining the error information in accordance with step S9. This is also designed to store the error information in the log file in accordance with step S10; alternatively, a logging unit can also be provided.

In addition, as part of the control device 21, there is also an intervention unit 29 for checking intervention conditions and for performing the corresponding interventions in accordance with steps S11 and S12, and a user interaction unit 30 for receiving user inputs and for outputting representations and/or notifications. Finally, a couch control unit 31 for driving the patient couch 1 (or actuators that propel the couch) is also provided for the travel into and out of the patient bore 2, in particular also in accordance with step S4.

Since the control device 21 is designed also to control the other operation of the magnetic resonance device 16, corresponding further functional units are also provided but are not shown here.

Although the disclosure has been illustrated and described in detail using the preferred exemplary aspect, the disclosure is not limited by the disclosed examples, and a person skilled in the art can derive other variations therefrom without departing from the scope of protection of the disclosure.

Independent of the grammatical term usage, individuals with male, female, or other gender identities are included within the term.

The invention claimed is:

1. A method for operating a magnetic resonance device that includes a main magnet unit having a main magnet to produce a main magnetic field and a patient bore, wherein field lines of the main magnetic field in a homogeneity volume in the patient bore run in a field direction, a patient couch to move a patient into the patient bore along a z-direction, which corresponds to a longitudinal direction of the patient couch, wherein, assigned to the patient couch, is a position determination device to determine a couch position along the z-direction, at least one local coil arrangement placeable on the patient and/or the patient couch, wherein the local coil arrangement has a magnetic field sensor to measure measurement values at least of a magnetic field strength of the main magnetic field, and a control device to determine first position information for the local coil arrangement, which first position information specifies a first measurement position by aligning a first measurement value from the magnetic field sensor with a main magnetic field map at least outside the patient bore, wherein the method comprises:

acquiring at a first couch position of the patient couch the first measurement value from the magnetic field sensor outside the patient bore at the first measurement position of the local coil arrangement, and determining the first position information;

acquiring at a second couch position of the patient couch a second measurement value from the magnetic field sensor during or after conclusion of travel by the patient couch into the patient bore at a second measurement position of the local coil arrangement, which second measurement position differs from the first measurement position;

determining at least one reference value, which specifies an expected main magnetic field at the second measurement position, wherein the second measurement position is determined from the first position information and a displacement distance of the patient couch between the first and second couch positions given by the position determination device; and determining error information, which indicates a potential measurement error, by comparing the second measurement value with the reference value, wherein in the comparison, determining an absolute or relative deviation of the second measurement value from the reference value, wherein a measurement error is detected if the deviation exceeds a limit value.

2. The method of claim 1, further comprising:
determining a first of the at least one reference value from the main magnetic field map at the determined second measurement position.

3. The method of claim 1, further comprising:
correcting the main magnetic field map before use based on a current calibration frequency measured by a magnetic resonance measurement.

4. The method of claim 1, further comprising:
if the second measurement position lies inside the homogeneity volume, determining at least a second of the at least one reference values from a calibration frequency, or measuring a current calibration frequency by a magnetic resonance measurement, which frequency corresponds to the magnetic resonance frequency in the homogeneity volume.

5. The method of claim 1, further comprising:
when using the second reference value, determining a relative deviation for the second reference value.

6. The method of claim 1, further comprising:
when the error information indicates a measurement error, outputting a visual and/or acoustic notification about the measurement error and/or logging the error information.

7. The method of claim 1, further comprising:
after a user has selected one of the at least one local coil arrangements, this is arranged in an isocenter of the magnetic resonance device, which is located in the homogeneity volume, by moving in the patient couch on based on the first position information for this local coil arrangement.

8. A magnetic resonance device, comprising:
a main magnet unit having a main magnet to produce a main magnetic field, and having a patient bore, wherein the field lines of the main magnetic field in a homogeneity volume in the patient bore run in a field direction;

a patient couch to move a patient into the patient bore along a z-direction, which corresponds to a longitudinal direction of the patient couch, wherein, assigned to the patient couch, is a position determination device to determine a couch position along the z-direction;

at least one local coil arrangement placeable on the patient and/or the patient couch, wherein the local coil arrangement has a magnetic field sensor to measure measurement values at least of a magnetic field strength of the main magnetic field; and a control device to determine first position information for the local coil arrangement, which first position information specifies a first measurement position, by aligning a first measurement value from the magnetic field sensor with a main magnetic field map at least outside the patient bore, wherein the control device is designed to perform a method of claim 1.

9. A non-transitory electronically readable data storage medium storing a computer program which, upon execution on a control device of a magnetic resonance device, causes the control device to perform the method of claim 1.

10. The method of claim 7, further comprising:
determining the error information for each user selection and positioning of a local coil arrangement for all the at least one local coil arrangement.

* * * * *